United States Patent
Sohling et al.

(10) Patent No.: US 9,677,027 B2
(45) Date of Patent: Jun. 13, 2017

(54) COMPOSITION FOR ENZYMATIC OIL DEGUMMING

(71) Applicant: CLARIANT PRODUKTE (DEUTSCHLAND) GMBH, Frankfurt am Main (DE)

(72) Inventors: Ulrich Sohling, Freising (DE); Paul Bubenheim, Hamburg (DE); Kirstin Suck, Munich (DE)

(73) Assignee: CLARIANT PRODUKTE (DEUTSCHLAND) GMBH, München (DE)

( * ) Notice: Subject to any disclaimer, the term of this patent is extended or adjusted under 35 U.S.C. 154(b) by 0 days.

(21) Appl. No.: 14/379,010

(22) PCT Filed: Feb. 18, 2013

(86) PCT No.: PCT/EP2013/053199
§ 371 (c)(1),
(2) Date: Aug. 15, 2014

(87) PCT Pub. No.: WO2013/121047
PCT Pub. Date: Aug. 22, 2013

(65) Prior Publication Data
US 2015/0017708 A1    Jan. 15, 2015

(30) Foreign Application Priority Data
Feb. 17, 2012   (DE) .................. 10 2012 003 031

(51) Int. Cl.
*C11B 3/00* (2006.01)
*C11B 3/04* (2006.01)

(52) U.S. Cl.
CPC ............. *C11B 3/003* (2013.01); *C11B 3/001* (2013.01); *C11B 3/008* (2013.01); *C11B 3/04* (2013.01); *C12Y 301/01004* (2013.01); *C12Y 301/01032* (2013.01); *C12Y 301/04003* (2013.01); *C12Y 301/04004* (2013.01)

(58) Field of Classification Search
None
See application file for complete search history.

(56) References Cited

U.S. PATENT DOCUMENTS

| | | | |
|---|---|---|---|
| 4,803,016 A | 2/1989 | Binderman et al. | |
| 5,175,210 A | 12/1992 | Machado | |
| 5,264,367 A | 11/1993 | Aalrust et al. | |
| 7,226,771 B2 | 6/2007 | Gramatikova et al. | |
| 2005/0059567 A1 | 3/2005 | Showell et al. | |
| 2005/0130281 A1* | 6/2005 | Both ................... | B01D 61/142 435/134 |
| 2006/0030012 A1* | 2/2006 | Kellens ................. | A23J 7/00 435/134 |
| 2010/0209968 A1* | 8/2010 | Akers ................... | C12N 11/08 435/68.1 |
| 2011/0093965 A1 | 4/2011 | O'Donoghue et al. | |

FOREIGN PATENT DOCUMENTS

| | | | | |
|---|---|---|---|---|
| CN | 1935962 A | 3/2007 | | |
| CN | 101659899 A | 3/2010 | | |
| EP | 0070269 A2 | 1/1983 | | |
| EP | 0513709 B1 | 3/1995 | | |
| EP | 13166529 | 11/2014 | | |
| GB | 1440462 A * | 6/1976 | ............ | C11B 3/003 |
| WO | 2008024840 A2 | 2/2008 | | |
| WO | WO 2008094847 A1 * | 8/2008 | ............ | C11B 3/003 |
| WO | 2009081094 A2 | 7/2009 | | |
| WO | 2012079663 A1 | 6/2012 | | |
| WO | 2013121047 A1 | 8/2013 | | |

OTHER PUBLICATIONS

Dijkstra, A.J. (2010), Enzymatic degumming. Eur. J. Lipid Sci. Technol., 112: 1178-1189 (Abstract).
Dijkstra, A.J. (2009), Recent developments in edible oil processing. Eur. J. Lipid Sci. Technol. 2009, 111, 857-864.
De Maria, V.O. (2007), Phospholipases and their industrial applications. Applied Microbiology and Biotechnology, vol. 74, Issue 2, pp. 290-300 (Abstract).
Selmair, Patrick L., et al. Molecular structure and baking performance of individual glycolipid classes from lecithins, Journal of agricultural and food chemistry, Jun. 24, 2009 (Abstract), 2 copies provided.
Claytou, T.A., Identification of wheat flour lipids by thin-layer chromatography. J. Chromatog., 47 (1970) 277-281) (Abstract).
Faber, K., Biotransformations in Organic Chemistry. A Textbook, 6th ed. 2011. 6th revised and corrected edition, XI, 423 p. 347 illus. (Abstract).
Scholfield, C.R., Composition of Soybean Lecithin, Northern Regional Research Center, Science and Education Adminstration, Agricultural Research, U.S. Department of Agriculture, Peoria, IL 60604 (Abstract).
Wiley-VCH, Whitehurst, Robert J. (ed.), Emulsifiers in Food Technology (Abstract), (2004)
H. Dominguez, et al.; "Oil extractability from enzymatically treated soybean and sunflower: range of operational variables;" Food Chemistry, 1993, pp. 277-284, vol. 46.

(Continued)

*Primary Examiner* — Renee Claytor
*Assistant Examiner* — Michelle F Paguio Frising
(74) *Attorney, Agent, or Firm* — Gianna J. Arnold; Saul Ewing LLP

(57) ABSTRACT

The invention relates to a composition comprising at least one phospholipid-cleaving enzyme. The invention further relates to a method for degumming raw oils using the composition according to the invention and to the use of the composition according to the invention to degum raw oils.

12 Claims, 4 Drawing Sheets

(56) References Cited

OTHER PUBLICATIONS

Figure 1:
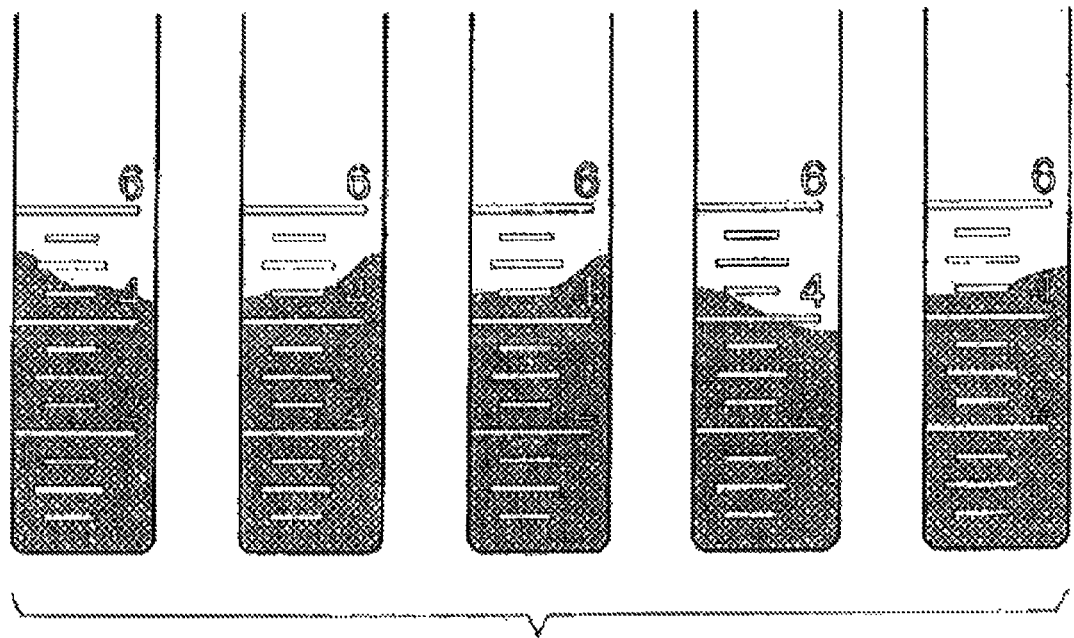

Michael Bokisch; "Fats and Oils Handbook;" AOCS Press, Champaign, Illinois, 1998, pp. 428-444.
K. Nielsen; "The Composition of the Difficulty Extractable Soybean Phosphatides;" J. Am. Oil. Chemists' Soc., May 1960, vol. 37, pp. 217-219.

* cited by examiner

COMPOSITION FOR ENZYMATIC OIL DEGUMMING

CROSS REFERENCE TO RELATED APPLICATIONS

This application claims the priority of PCT/EP2013/053199, filed on Feb. 18, 2013, which claims priority to European Application No. 102012003031.2, filed Feb. 17, 2012, the entire contents of each of which are hereby incorporated in total by reference.

The invention relates to a composition comprising at least one phospholipid-cleaving enzyme. The invention relates further to a method for degumming crude oils using the composition according to the invention, and to the use of the composition according to the invention for the degumming of triglycerides, in particular of crude vegetable oils.

Crude oils contain phosphatides, protein- and carbohydrate-containing substances, vegetable gums and also colloidal compounds, which reduce the life of the oil considerably. These substances must therefore be removed.

In the following text, gum phase/gums is understood as meaning the entire group of those substances, which are obtained from the oil as a heavy phase after treatment with an acid-containing and/or aqueous solution (Bokisch, M, Nahrungsfette and -öle, Handbuch der Lebensmittel-Technologie, Ulmer Verlag, 342-433).

The refining of vegetable oils is understood as meaning the removal of undesirable associated substances. A distinction is made between chemical and physical refining. Chemical refining consists of the processes 1. degumming, 2. neutralization, 3. bleaching, 4. deodorization. In the degumming, phospholipids and metal ions are removed from the oil. Neutralization serves to extract the fatty acids. In the bleaching, the colorants, further metal ions and residual gums are removed. The deodorization is a steam distillation, in which further compounds which impair the odor and taste of the oil are removed. In physical refining, the deacidification is carried out together with the deodorization at the end of the refining process.

The degumming of the oils can be carried out by extracting the phospholipids with water or an aqueous solution of an acid that complexes $Ca^{2+}$ and $Mg^{2+}$ ions, such as, for example, citric acid or phosphoric acid. An aqueous, so-called pre-degumming is frequently carried out first, by means of which the water-soluble phospholipids are removed.

These are referred to as hydratable phospholipids. The subject of hydratable and non-hydratable phospholipids is described, for example, in Nielsen, K., Composition of difficultly extractable soy bean phosphatides, J. Am. Oil. Chem. Soc. 1960, 37, 217-219 and A. J. Dijkstra, Enzymatic degumming, Eur. J. Lipid Sci. Technol. 2010, 112, 1178-1189. These are in particular phosphatidyl-choline and phosphatidyl-inositol. Treatment with dilute aqueous calcium- and magnesium-complexing acids, such as, for example, citric acid or phosphoric acid, has the result according to the prior art that non-hydratable phospholipids are converted into hydratable phospholipids. It is assumed that the mechanism of this reaction is based on the fact that calcium ions, which bridge and stabilize various phospholipid molecules, such as, for example, phosphatidic acids on the phosphate groups, are removed from the oil. This leads to improved extraction of these phospholipids with water. Although sufficiently good degumming is achieved by aqueous pre-degumming and treatment with aqueous acids in the case of some oils, such as, for example, palm oil, these two extraction steps very often lead to an unsatisfactory reduction of the gums for other vegetable oil types, such as, for example, canola oil, rapeseed oil or soybean oil. A reduction of the phosphorus content to 10 ppm phosphorus or less in the oil is usually desired for foodstuffs applications (determined according to the prior art by ICP/AES analysis of the oil). Stricter requirements are made of the phosphorus content of the oil when the oils are used, for example, in the production of biodiesel. In that case, the phosphorus content of the biodiesel is limited to 5 ppm according to the EU standard, and it is advantageous to carry out the phosphorus reduction on the oil. Furthermore, a particularly low phosphorus content, that is to say a phosphorus content that is as low as possible and where possible is 0, is required when the oils, in further treatment steps, are either hydrogenated for use in foodstuffs, that is to say unsaturated fatty acids are converted into fatty acids, or when a hydrogenation is carried out according to the NExBTL process of Neste in such a manner that alkanes are obtained as the end product, that is to say a conventional biodiesel fuel but produced from vegetable oil is obtained. As stated above, these processes make extremely high requirements of a low phosphorus content in the oil, and the use of such processes will increase as the use of vegetable oils as raw materials for the chemical industry increases.

A further variant is so-called "caustic refining". This process is used to remove from the oil all the phospholipids, if possible, together with free fatty acids. This process is described, for example, in WO 08/094,847 of Bunge. In this process, the crude oil or oil pre-degummed with water is first mixed with small amounts of citric acid or phosphoric acid and stirred intensively. As already explained above, salts of non-hydratable phospholipids are thereby rendered more hydratable. Dilute sodium hydroxide solution is then added, wherein the amount is so calculated that a slight excess is obtained relative to the amount required for neutralization of the free fatty acid. The fatty acid salts are thereby formed. The mixture is then separated by sedimentation and subsequent centrifugation, and an aqueous fatty acid solution is obtained as residue, in which the phospholipids are also to be found. The oil is then subsequently washed again with softened water. The NaOH treatment has the disadvantage that saponification of the oil also occurs to some extent, as a result of which its yield is reduced.

According to the prior art, a further reduction of the phosphorus content in the oil can be achieved either by carrying out an adsorbent treatment with a bleaching earth or a special silica gel, or by degumming the vegetable oils enzymatically. The adsorbent treatment has the disadvantage that vegetable oil remains on the adsorbent after the adsorbent treatment, which reduces the oil yield of the refining process as a whole. In addition, the used bleaching earth represents "waste", for which possible methods of disposal must be found.

A further disadvantage of conventional oil degumming processes is that both the aqueous pre-degumming and the treatment with aqueous acids lead to oil losses, which arise because the phospholipids transferred into the water are emulsifiers which emulsify a small but nevertheless still substantial portion of the vegetable oil in the aqueous phase, so that vegetable oil is lost. These losses can be in the region of a few percent, based on the crude oil originally used. As a rule of thumb, with every two molecules of phospholipid, approximately one triglyceride molecule is emulsified (described in WO 08/094,847).

So-called enzymatic degumming avoids several of the disadvantages of the existing methods, or improves the extraction methods further. For example, no additional waste is formed as with the use of adsorbents, and it has been shown that oil losses can be reduced further in the case of enzymatic degumming.

So-called enzymatic degumming is effected in the prior art by the use of phospholipases, in particular phospholipase A1 and A2 or phospholipase C or a combination of phospholipases.

Phospholipases are enzymes belonging to the group of the hydrolases, which hydrolyse the ester binding of phospholipids. Phospholipases are divided into 5 groups according to their regioselectivity in the case of phospholipids:

Phospholipases $A_1$ ($PLA_1$), which cleave the fatty acid in the sn1-position with formation of the 2-lysophospholipid.

Phospholipases $A_2$ ($PLA_2$), which cleave the fatty acid in the sn2-position with formation of the 1-lysophospholipid.

Phospholipases C (PLC), which cleave a phosphoric acid monoester.

Phospholipases D (PLD), which cleave or replace the headgroup.

Phospholipases B (PLS), which cleave the fatty acid both in the sn1-position and in the sn2-position with formation of a 1,2-lysophospholipid.

These reactions always take place at the interface of aggregated substrates.

The use of phospholipases, especially phospholipase A, for the degumming of crude oils is protected, for example, in EP 0513709 B1 (so-called Enzymax process of Lurgi, Frankfurt). It is assumed that the cleavage of a fatty acid leads to a lysolecithin, which has a substantially lower emulsifying capacity for oil and also possesses substantially higher water solubility. As a result, the oil yield is improved and the water solubility of the difficultly hydratable phospholipids is improved. The article by Clausen, Enzymatic oil-degumming by novel microbial phospholipase, Eur. J. Lipid Sci. Technol. 103 (2001) 333-340 describes the development and use of a phospholipase A1 for enzymatic oil degumming and compares the use of phospholipase A1 with the use of phospholipase A2. The current state of the art relating to enzymatic oil degumming is summarized in the two articles by A. J. Dijkstra, Recent developments in edible oil processing, Eur. J. Lipid Sci. Technol. 2009, 111, 857-864 and the article by A. J. Dijkstra, Enzymatic degumming, Eur. J. Lipid Sci. Technol. 2010, 112, 1178-1189. The advantages and disadvantages of the individual phospholipases for enzymatic oil degumming are discussed therein, and the pre-treatment methods with different acids are also presented.

An alternative concept for oil degumming is represented by the systems of Danisco, in which a lipid acyltransferase is used. This enzyme also creates a lysophospholipid from a phospholipid, but it transfers the fatty acid residue to a sterol in the oil phase. The corresponding enzymes and methods for using those enzymes are described in WO 2006/008508 and WO 2009/081094.

From the point of view of oil yield, it would be most advantageous to use for the enzymatic degumming a highly active phospholipase C, which yields as product a diglyceride, which is soluble in the oil, and a phosphatidyl residue, such as, for example, phosphatidyl-choline (starting from lecithin), which is very readily water-soluble. Such enzymes have been described by Verenium in U.S. Pat. No. 7,226,771. In the review article by Dijkstra on the subject "Enzymatic degumming", it is mentioned as a disadvantage of this system that it does not convert all phospholipids but only lecithins, that is to say phosphatidyl-choline and phosphatidyl-inositol, while the difficultly hydratable ethanolamines and phosphatidic acids remain untouched. This disadvantage has led to phospholipase C being combined either with phospholipases A or with lipid acyltransferases in subsequent developments. A combination of phospholipases A with phospholipases C for oil degumming is described in WO 08/094,847. In that patent specification it is stated on the one hand that the mixture of phospholipase A and phospholipase C leads to a synergistic effect in the oil yield and on the other hand that it is thereby possible to establish very low phosphorus contents in the oil with compatible reaction times.

The combination of phospholipase C with lipid acyltransferases is described in WO 2009/081094. It is stated here too that the combination of the acyltransferase with the phospholipase C leads to an increase in the oil yield. A further variant of enzymatic oil degumming is enzymatic treatment of the separated gum phase after the oil has been degummed by conventional methods such as, for example, with water and/or citric acid. This treatment makes it possible to recover some of the vegetable oil emulsified in the gum phase. This method is also discussed, for example, in the review article A. J. Dijkstra, Enzymatic degumming, Eur. J. Lipid Sci. Technol. 2010, 112, 1178-1189 p. 1184. Corresponding methods are also described in the following patent specifications:

EP 01 624 047 describes the recovery of oil from the gum by the use of phospholipolytic agents, wherein the phospholipolytic agents can be both acids and phospholipases.

As well as describing the aspects mentioned above, WO 2009/081094 also describes the enzymatic treatment of the separated gum phase with acyltransferase and mixtures of acyltransferase and phospholipase C.

WO 2009/088980 describes the enzymatic treatment of the gums with phospholipase C and phospholipase A.

Finally, the aspect of the sustainability of the use of phospholipases as compared with other degumming methods is described in the article L. De Maria & J. Vind & K. M. Oxenbøll & A. Svendsen & S. Patkar, Phospholipases and their industrial applications, Appl Microbiol Biotechnol (2007) 74:290-300 p. 96 and 97. Using the example of an oil mill which was converted from a conventional degumming process to a process using phospholipase A and in which 266,000 t of soybean oil are purified per year, it has been shown that 120,000 GJ of energy and 12,000 t of $CO_2$ equivalents can be saved per year. The $CO_2$ equivalents saved correspond to the emissions of 1600 average terrestrials.

On account of the worldwide increase in the consumption of edible oil and the ever increasing use of vegetable oils as raw materials for the chemical industry and as a fuel, there is a continued further need to improve further the degumming of vegetable oils and in particular the enzymatic degumming of vegetable oils. The inventors of the present application have therefore set themselves the object of developing compositions for enzymatic degumming with which the phosphorus content of the oil to be degummed is reduced further, the oil losses are reduced and/or rates of reaction of the enzymatic degumming are increased. At the same time, these compositions are additionally to allow the method to be carried out economically on an industrial scale.

That object has been achieved by a composition which a first enzyme component comprising at least one phospholipid-cleaving enzyme and a second enzyme component comprising at least one non-phospholipid-cleaving enzyme. The non-phospholipid-cleaving enzyme is preferably a sugar-cleaving enzyme, which is also known as a glycoside-cleaving enzyme or glycosidase. The expression "glycoside-cleaving enzyme" also includes all further enzymes from other enzyme classes which possess a subsidiary glycoside-cleaving activity.

Within the meaning of the present invention, the expression "first enzyme component" is understood as meaning any composition that comprises or consists of at least one phospholipid-cleaving enzyme.

The "phospholipid-cleaving enzyme" can be a phospholipase which is capable of cleaving either a fatty acid residue or a phosphatidyl residue or a headgroup from a phospholipid. Furthermore, it can also be a so-called acyltransferase, in which the cleavage of the fatty acid residue is combined with a transfer of the residue, followed by an ester formation, with a free sterol in the oil phase.

In a preferred embodiment, the present invention therefore relates to a composition in which the first enzyme component is selected from the group consisting of phospholipase A1, phospholipase A2, phospholipase C, phospholipase B, phospholipase D and acyltransferase. Typical enzymes from this group which are available on the market are Lecitase®Ultra from Novozymes®, a phospholipase A1, Lecitinase® from Novozymes, a phospholipase A2, Rohalase® MPL, a phospholipase A2 from AB Enzymes, Darmstadt (D), Purifine®, a phospholipase C from Elementis, San Diego USA, Lysomax®, acyltransferase from Danisco. It is also possible for a combination of two or more of the above-mentioned phospholipid-cleaving enzymes to be used in the first enzyme component. The enzymes can originate from any desired organism (e.g. can also be isolated from a thermophilic organism) or from a synthetic source. It is also possible within the scope of the present invention that enzymes which are of the same type but originate from different sources or species are used in the first enzyme component. Also included are chimeric fusion proteins produced by recombinant methods from two or more different species having enzymatic activity.

Within the meaning of the present invention, the expression "second enzyme component" is understood as meaning any composition which comprises or consists of at least one enzyme which does not act on phospholipids, that is to say does not alter them in terms of their chemical structure.

In a preferred embodiment, the present invention therefore relates to a composition in which the second enzyme component is selected from the group of the hydrolases which cleave glycoside bonds, comprising, for example, amylase, amyloglucosidase, laminaranase, glucoamylase, glucosidase, galactosidase, glucanase, mannanase, pectinase, cellulase, xylanase, pullulanase, arabinase, dextranase. It is also possible for a combination of two or more of the above-mentioned glycoside-cleaving enzymes to be used in the second enzyme component. The enzymes can originate from any desired organism (e.g. can also be isolated from a thermophilic organism) or from a synthetic source. It is also possible within the scope of the present invention that enzymes which are of the same type but originate from different sources or species are used in the second enzyme component. Also included are chimeric fusion proteins produced by recombinant methods from two or more different species having enzymatic activity.

In a preferred embodiment of the present invention, the composition is used in a method for degumming vegetable oils or for reducing the emulsifiability of vegetable oils in aqueous phases.

The expression "pre-degumming" or "wet degumming" is understood as meaning a treatment of the crude oil with water or an aqueous acid solution in order to remove water-soluble phospholipids from the oil as far as possible. A pre-degumming or wet degumming can optionally also include, after the addition of acid, the addition of alkali in order to neutralize the acid. Before the enzyme is added, the aqueous phase is separated off. After a pre-degumming, the phosphorus content in the crude oil is lowered by approximately 500-1500 ppm, for example for soybean and rapeseed to less than 200 ppm in the pre-degummed oil. By means of the pre-degumming, lecithin can be obtained from the resulting gum phase, for example, or the gum phase can be worked up as a feed. The disadvantage of separating the aqueous phase, or lowering the phosphorus content, is, however, a loss of yield in respect of the oil. The phosphatides transferred into the aqueous phase have an emulsifying action and result in part of the oil being emulsified in the aqueous phase and separated off therewith. The oil can then be treated further enzymatically (wherein the enzymes must be separated off in a further step).

The term "pre-conditioning" of the oil is understood in the following application as meaning the addition of water or an aqueous acid solution to the untreated crude oil. A pH at which the subsequent enzymatic reaction takes place is then established by addition of alkali, for example sodium hydroxide solution. Ideally, the optimal pH for the enzyme reaction is established. For the phospholipid-cleaving enzymes, that is a pH of 4.5. However, this is not followed by the separation of the aqueous phase but by the immediate addition of the enzymes. The gums that are present thus remain for the time being in the oil or in the emulsion. Separation of the aqueous phase and thus of the enzymes only takes place after the enzymes have acted on the (optionally pre-conditioned) crude oil.

In a preferred embodiment, an addition of water or an aqueous acid solution and optionally of alkali for neutralizing the acid to the crude oil can be carried out within the context of a pre-conditioning, but separation of the aqueous phase before the addition of the enzymes (within the context of a wet pre-degumming) is omitted. By omitting the separation step before the addition of the enzymes, it is possible to increase the oil yield. An increase of the oil yield by one percentage point is of enormous economic importance, because that percent corresponds to approximately 400,000 t of oil, based on the annual production of soybean oil. The method according to the invention accordingly permits the direct use of crude oils from soybean or rapeseed with phosphorus contents of from 500 to 1500 ppm phosphorus. Moreover, it represents a simplification of the method because the separation step before addition of the enzymes is omitted.

When adding water, the following is to be noted: in order to remove the phosphatides from the oil, approximately 1% by volume of water, based on the volume of oil, is required to remove approximately 400 ppm of phosphorus. Accordingly, the addition of approximately 5% by volume of water, based on the volume of oil, is sufficient to free even an oil having a high phosphorus content completely of phosphorus. However, such a procedure has the effect that the method becomes uneconomical, because ever greater reaction volumes have to be provided. Moreover, a larger added water volume means a higher outlay in terms of separation and a lower oil yield; less added water accordingly also means a higher oil yield. In general, therefore, not more than 4% by volume of water, preferably not more than 3% by volume of water, in each case based on the volume of oil, should be added to the oil.

In a further preferred embodiment, no additional emulsifiers, such as, for example, sodium dodecyl sulfate (SDS), are added in the refining step—apart from the emulsifiers, such as, for example, lecithin, already present in the oil. The method according to the invention is likewise preferably carried out without the addition of salts, such as, for example, calcium chloride ($CaCl_2$).

In a preferred embodiment, the enzyme activity of the enzyme/enzymes of the first enzyme component is chosen in the range of from 0.01 to 6 units/g oil, more preferably in the range of from 0.1 to 3 units/g oil oil, particularly preferably in the range of from 0.2 to 2.5 units/g oil and most preferably in the range of from 0.3 to 1 unit/g oil. In a further preferred embodiment, the enzyme activity of the second enzyme component is chosen in the range of from 0.01 to 6 units/g oil, preferably from 0.1 to 3 units/g oil, and particularly preferably in the range of from 0.2 to 2.5 units/g oil, and most preferably in the range of from 0.3 to 1 unit/g oil. (Unit: international unit for enzyme activity; 1 unit corresponds to the substrate conversion of 1 µmol/min).

Particular preference is given within the scope of the present invention to compositions in which the ratio of the enzyme activity of the first enzyme component to the enzyme activity of the second enzyme component is in the range of from 0.01:6 units/g oil to 6:0.01 units/g oil, preferably in the range of from 0.1:3 units/g oil to 3:0.1 units/g oil. It is also preferred if the proportion of the first enzyme component and the proportion of the second enzyme component are equal, for example both components are chosen in the range of from 0.1 to 0.5 unit/g oil, preferably in the range of from 0.2 to 0.3 unit/g oil.

By maintaining the ratio according to the invention of the phospholipid-cleaving enzyme to the glycoside-cleaving enzyme, the volume of the gum phase can be reduced. This means an increase in the oil yield.

The enzymes of the first and/or second enzyme component can, for example, be lyophilized and used in solution in corresponding enzyme buffer (standard buffers for each enzyme are described in the literature), for example citrate buffer 0.1 M, pH 5 or acetate buffer 0.1 M, pH 5. In a preferred embodiment, the enzymes are taken up in enzyme buffer and added to the crude oil. In order to achieve better solubility of the enzymes—in particular in the mixtures containing phospholipids—the addition of organic solvents is also possible. These are used, for example, in the separation of the phospholipids and are described in the literature. Preference is given to the use of non-polar organic solvents such as, for example, hexane or acetone or mixtures, preferably in an amount of from 1 to 30% by weight (examples of possible solvents are described in EP 1531182 A2).

In a further preferred embodiment, the first and/or second enzyme component is used in immobilized form. Because the phospholipid-cleaving enzymes in particular are special enzymes whose price, measured in comparison with bulk enzymes, such as, for example, carbohydrate-degrading enzymes (amylases, glucosidases), is relatively high, it is preferred within the scope of the present invention if at least the phospholipid-cleaving enzyme/s of the composition is/are used in immobilized form. Preferred support materials within the scope of the present invention are inorganic support materials, such as, for example, silica gels, precipitated silicas, silicates or aluminosilicates, and organic support materials, such as, for example, methacrylates or ion-exchange resins. The support materials facilitate the recyclability of the (relatively expensive) enzymes from the oil/water emulsion in a following method step and contribute towards the economy of the method.

In an embodiment which is likewise preferred, the first and/or second enzyme component comprises one or more further constituents, particularly preferably selected from the group consisting of citrate buffers and acetate buffers.

In particularly preferred embodiments of the composition according to the invention, which do not limit the scope of the present invention in any way, the first enzyme component comprises at least one enzyme selected from the group consisting of phospholipase A1, phospholipase A2 and phospholipase C, and the second enzyme component preferably comprises at least one enzyme selected from the group consisting of α-amylase and mannanase, wherein the enzymes are particularly preferably lyophilized enzymes which are present in a buffer selected from the group consisting of citrate buffer or acetate buffer. In addition, it is most preferred if at least the enzyme of the first enzyme component is bonded adsorptively or covalently to a support which is preferably selected from the group consisting of inorganic support materials such as, for example, silica gels, precipitated silicas, silicates or aluminosilicates and organic support materials such as, for example, methacrylates or ion-exchange resins. It is likewise preferred in this particularly preferred embodiment if the ratio of the enzyme activity of the first enzyme component to the enzyme activity of the second enzyme component is in the range of from 0.01:6 units/g oil to 6:0.01 units/g oil, preferably in the range of from 0.1:3 units/g oil to 3:0.1 units/g oil. It is also preferred if the proportion of the first enzyme component and the proportion of the second enzyme component are equal, for example both components are chosen in the range of from 0.1 to 0.5 unit/g oil, preferably in the range of from 0.2 to 0.3 unit/g oil.

The inventors of the present composition have found, surprisingly, that a combination of the enzyme components (first and second enzyme component) defined above reduces the emulsifiability of vegetable oil in aqueous phases particularly efficiently and effectively. The composition according to the invention can be used particularly advantageously for the degumming of crude vegetable oil or also for the purification of vegetable oil gum. The gum phase can be obtained, for example, by a conventional degumming method (as is likewise described in the scope of the application) or by the method according to the invention, when it is used for the degumming of crude vegetable oil.

The present invention therefore relates in a further aspect to the use of the composition as defined in greater detail above for reducing the emulsifiability of vegetable oil in aqueous phases.

In addition, the present invention relates also to a method for reducing the emulsifiability of vegetable oil in aqueous phases, comprising the steps
 a) contacting the crude vegetable oil with a composition as defined above;
 b) separating the gums from the vegetable oil.

Surprisingly, it has been found that it is possible, by means of the combination of phospholipid-cleaving enzyme(s) of the first enzyme component with glycoside-cleaving enzyme(s) of the second enzyme component, to reduce the phospholipid content of the crude oil further as compared with the use of phospholipid-cleaving enzyme alone, to increase the oil yield, to increase the rate of reaction in the enzymatic degumming, to lower the gum volume and/or to improve the separability of the gum phase that is formed.

The method of the present invention is particularly advantageous because, by using a further enzyme component (second enzyme component) which comprises at least one glycoside-cleaving enzyme, the cleavage of further components present in the gum phase can take place and the action of the phospholipid-cleaving enzyme is accordingly improved. By using the second enzyme component it is, for example, possible to lower the viscosity of the oil gum phase, to increase the mobility of the phospholipids as a result of the cleavage of interfering components, or to achieve better accessibility of the phospholipids. The accessibility of those phospholipid molecules that are located at the gum phase/oil interface to the phospholipid-cleaving enzyme is probably also increased.

For example, by using glycosidases it is possible to cleave glycolipids. The class of the glycolipids includes a large number of compounds. According to the literature, however, the gum phase, or vegetable phospholipids, contain(s) especially steryl glycosides, cerebrosides and galactosyl lipids (Selmair, P. L., Koehler, P. in Molecular Structure and Baking Performance of Individual Glycolipid Classes from Lecithins, J. Agric. Food Chem. 2009, 57, 5597-5609). For example, it has been shown that defatted soybean lecithin contains up to 10% glycolipids. This is also described in another literature reference, namely in Bueschelberger, H. G., Lecithins, Emulsifiers in Food Technology, Whitehurst, R. J., Ed.; Blackwell Publishing: Oxford, U.K., 2004; pp. 1-10, and also by Clayton, T. A., Identification of wheat flour lipids by thin-layer chromatography, J. Chromatogr. 1970, 47, 277-281. In a further reference by Pardun, H., Eigenschaften der Pflanzenlecithine, in Pflanzenlecithine; Pardun, H., Ed.; Verlag für chemische Industrie H. Ziolkowsky K G: Augsburg, Germany, 1988; pp. 195-202, a range of from 6.5 to 11% is indicated. It is supposed that the cleavage of these molecules into a polar residue and a water-soluble headgroup, which can optionally be dissolved in oil again, contributes towards the phospholipids being present in more concentrated form in the micelles of the gum phase and therefore being able to be converted more quickly by the phospholipases. The same consideration applies for phospholipids at the oil/gum interface.

The reduced emulsifying capacity of the lipids of the gum phase after treatment with the glycoside-cleaving enzyme additionally contributes towards the oil yield being able to be increased further. The effect of the polysaccharide- and cell-wall-constituent-cleaving enzymes can be explained as follows: the phospholipids become better accessible to the phospholipases, and the rate of reaction may also increase. The presence of carbohydrates is confirmed by analyses of soybean lecithin, as published, for example, by Scholfield, C. R., Composition of Soybean Lecithin, JAOCS, Vol. 58, no. 10 (October 1981), pp. 889-892, that the crude lecithin also contains carbohydrates.

Thus, for example, cell wall pectins and polysaccharides to a certain extent and further cell wall constituents have a pronounced thickening action. The increase in viscosity caused thereby can in some cases lower the rate of reaction of phospholipases. By cleaving these cell wall constituents and/or polysaccharides into readily water-soluble fragments which do not increase the viscosity, the effect of the added enzymes on the effectiveness of phospholipases can be explained.

By combining, according to the invention, phospholipid-cleaving enzymes with glycoside-cleaving enzymes it is possible to reduce the added amount of the phospholipid-cleaving enzymes, such as, for example, the phospholipase A1 or A2 optionally combined with phospholipase C, and thus, as well as achieving the advantages listed above for the process, also save costs. The glycoside-cleaving enzymes which are combined with the phospholipid-cleaving enzymes are generally less expensive enzymes than, for example, phospholipases and are obtainable in large amounts. In combination with an advantageous reaction procedure, that is to say process conditions which are matched to the particular enzymes used, the method according to the invention can be further improved in terms of duration and also energy and raw material consumption.

According to the invention there are preferably used: phospholipase $A_1$ which originates from *Thermomyces lanuginosus, Fusarium oxysporium, Aspergillus oryzae, Bacillus cereus, Bacillus subtilis, Clostridium perfringens, Listeria monocytogenes, Pseudomonas* species, porcine pancreas or bovine pancreas; and/or independently phospholipase $A_2$ which originates from porcine pancreas, bovine pancreas, *Streptomyces violaceoruber, Naja mossambica, Thermomyces lanuginosus, Fusarium oxysporium, Aspergillus oryzae, Bacillus cereus, Bacillus subtilis, Clostridium perfringens, Listeria monocytogenes* or *Pseudomonas* species; and/or independently phospholipase C which originates from *Bacillus cereus, Clostridium perfringens, Listeria monocytogenes, Thermomyces lanuginosus, Fusarium oxysporium, Aspergillus oryzae, Bacillus cereus* or *Pseudomonas* species; and/or independently phospholipase B which originates from *Thermomyces lanuginosus, Fusarium oxysporium, Aspergillus oryzae, Bacillus cereus, Bacillus subtilis, Clostridium perfringens, Listeria monocytogenes, Pseudomonas* species, porcine pancreas or bovine pancreas.

Particular preference is given to phospholipase $A_1$ from *Thermomyces lanuginosus* or *Fusarium oxysporium*, and/or independently phospholipase $A_2$ from porcine pancreas, bovine pancreas, *Streptomyces violaceoruber* or *Naja mossambica*, and/or independently phospholipase C from *Bacillus cereus, Clostridium perfringens* or *Listeria monocytogenes*.

As regards the glycoside-cleaving enzymes, preference is given to those which cleave $\alpha(1\text{-}4)$glycosidic, $\alpha(1\text{-}2)$glycosidic, $\alpha(1\text{-}6)$glycosidic, $\beta(1\text{-}3)$glycosidic, $\beta(1\text{-}4)$glycosidic and/or $\beta(1\text{-}6)$glycosidic bonds. Preference is further given to amylases, in particular $\alpha$-amylases, $\beta$-amylases, $\gamma$-amylases and isoamylases, and also to mannanases.

As regards the amylases and mannanases, preference is given to those from *Bacillus* or *Pseudomonas* or fungal species or from pancreas, in particular those from *Bacillus sp., Bacillus subtilis, Bacillus licheniformis, Bacillus megaterium, Bacillus amyloliquefaciens, Bacillus stearothermophilus, Pseudomonas aeroginosus, Pseudomonas fluorescens, Aspergillus oryzae, Aspergillus niger* or *Trichoderma reesei*. In the case of the mannanases, a mannanase from *Trichoderma reesei* is particularly preferred.

For the degumming of soybean oil, particular preference is given to a combination of the phospholipase $A_1$ from *Thermomyces lanuginosus* or *Fusarium oxysporium* and/or the phospholipase $A_2$ from porcine pancreas or bovine pancreas with an $\alpha$-amylase from *Bacillus* species and/or mannanase from *Trichoderma* species. For the degumming of rapeseed oil, particular preference is given to a combination of the phospholipase $A_1$ from *Thermomyces lanuginosus* or *Fusarium oxysporium* and/or the phospholipase $A_2$ from porcine pancreas or bovine pancreas with an $\alpha$-amylase from *Bacillus* species or *Aspergillus* species.

The expression "crude vegetable oil" is understood as meaning any crude oil of vegetable origin. Preferred crude oils within the scope of the present invention are crude soybean oil, crude rapeseed oil, crude sunflower oil, crude olive oil, crude palm oil, crude jatropha oil, crude algae oil, crude cameline oil, crude cottonseed oil, in particular crude soybean oil, crude rapeseed oil, crude jatropha oil, crude cameline oil and crude sunflower oil. The term "crude" refers to the fact that the oil has not yet been subjected to a degumming, neutralizing, bleaching and/or deodorizing step. It is also possible within the scope of the method according to the invention that a mixture of a plurality of crude oils is used or pre-treated, for example pre-conditioned or pre-degummed oils are treated with the enzymes.

"Contacting" can be carried out within the scope of the method according to the invention in any manner known to the person skilled in the art as being suitable for the purpose according to the invention. Preferred types of contacting is mixing of the crude oil and the composition according to the invention.

After contacting of the crude oil with the composition according to the invention, the mixture of crude oil and composition is preferably stirred, particularly preferably with a blade stirrer at from 200 to 800 rpm, preferably from 250 to 600 rpm and most preferably at from 300 to 500 rpm.

The temperature of the mixture during contacting is preferably in the range of from 15 to 99° C., more preferably in the range of from 20 to 95° C., more preferably from 22 to 80° C., likewise preferably from 25 to 65° C., more preferably from 27 to 55° C. and most preferably from 30 to 45° C. The temperature of the mixture must always be chosen so that the denaturing temperature of the enzymes is not exceeded, the temperature of the mixture is preferably at least 5° C. below the denaturing temperature of the enzymes or the lowest denaturing temperature of the enzymes. Wherein when enzymes that have been isolated from thermophilic organisms are used, higher temperatures are in principle to be preferred. If one or more thermally stable enzymes are used within the scope of the present invention, the process temperature is preferably in the range of from 80 to 120° C., more preferably in the range of from 85 to 100° C. The use of thermally stable enzymes has the advantage that an increased method temperature can accordingly be chosen, whereby the viscosity of the vegetable oil is reduced and the method as a whole can be shortened—also on account of an increased rate of reaction of the enzymes. Furthermore, in the case of a pre-treatment, which is advantageously likewise carried out at elevated temperatures, subsequent cooling below a lower denaturing temperature of the enzymes used is unnecessary. Overall, the use of thermally stable enzymes accordingly leads to a shortening of the method and a reduction in costs.

The duration of the contacting is preferably in the range of from 1 minute to 12 hours, more preferably from 5 minutes to 10 hours, likewise preferably from 10 minutes to 6 hours, more preferably from 20 minutes to 3 hours.

The pH of the mixture during the contacting is preferably in the range of from pH 3 to pH 7.5, more preferably in the range of from pH 4 to pH 6 and particularly preferably in the range of from pH 4.0 to pH 5.2.

Contacting of the crude vegetable oil with the first and second enzyme component of the composition according to the invention can take place simultaneously or in succession. Where contacting takes place in succession, it is preferred within the scope of the present invention if the crude vegetable oil is first contacted with the second enzyme component. Where the crude vegetable oil is contacted first with one enzyme component and then with the other enzyme component, it is particularly preferred if, after the addition of one component, the mixture is stirred for from 30 to 300 minutes, preferably from 60 to 240 minutes, likewise preferably from 70 to 120 minutes, before the other component is added.

"Separation" of the gums according to step b) of the method according to the invention can be carried out in any manner known to the person skilled in the art as being suitable for the purpose according to the invention. However, the separation preferably takes place by centrifugation or filtration, wherein centrifugation is preferred. In the case of centrifugation, a phase separation of the mixture takes place, so that the treated vegetable oil, the gums and the enzyme composition are present in separate phases which can easily be separated from one another.

In a preferred embodiment, the phase containing the gums and the phase containing the composition according to the invention are separated from the treated oil. It is particularly preferred if the first and/or second enzyme component is separated off at the same time as the gums.

After the separation, the enzymes can be regenerated or purified and, for example, used in a new purification process. In this case too, it is likewise advantageous to work with the compositions according to the invention again, either by using the other glycoside-cleaving enzymes directly in combination with immobilized phospholipases or lipid acyltransferases, or by using the composition according to the invention to remove the vegetable oil gum, which adheres, for example, to immobilized phospholipases, in order better to be able to reuse the immobilized enzymes in a new method.

A further preferred embodiment of the present invention relates additionally to a method as described above, further comprising the step c) again contacting the vegetable oil according to step b) with the first and/or second enzyme component.

"Contacting" preferably takes place under the same conditions as described above for step a) of the method according to the invention. In a particularly preferred embodiment, the first and/or second enzyme component is subjected to regeneration or purification before contacting is carried out again.

In a particularly preferred embodiment, the crude vegetable oil is contacted with water and/or acid before the contacting according to step a) of the method according to the invention. Preferred acids are calcium- and magnesium-complexing acids on their own or in combination, such as, for example, citric acid and phosphoric acid. This is referred to as so-called "pre-conditioning".

In a preferred embodiment of the method according to the invention, contacting with water takes place at a temperature of from 30° C. to 90° C. for from 15 to 60 minutes, preferably from 30 to 60 minutes, wherein a temperature of from 35 to 85° C. is preferred and a temperature of from 40 to 80° C. is particularly preferred. Contacting with acid, in particular citric acid or phosphoric acid, takes place within the scope of the method according to the invention preferably at a temperature of from 30° C. to 90° C. for from 5 to 60 minutes, preferably from 15 to 60 minutes, wherein a temperature of from 35 to 85° C. is preferred and a temperature of from 40 to 80° C. is particularly preferred. In a preferred embodiment, the acid treatment is followed by a neutralizing step with a corresponding base in order to achieve a pH of from 3.5 to 8.0, preferably from 4 to 7. It is preferred according to the method of the present invention if the composition according to the invention is added directly to the vegetable oil without a separating step being carried out beforehand.

Before the addition of the phospholipase(s) and/or further enzymes it must, however, be ensured that the reaction temperature does not exceed the optimum temperature range of the enzyme, in order to prevent denaturing of the enzyme. Temperatures of from 35 to 65° C., preferably from 45 to 55° C., are suitable, whereby the use of enzymes from thermophilic organisms, that is to say enzymes that are particularly stable to temperature, can permit use at from 80 to 100° C., so that a temperature reduction does not have to take place between contacting of the crude vegetable oil with water and/or acid and contacting with the composition according to the invention. An increase in temperature stability can also be achieved by immobilizing the enzymes of the enzyme components. Because many enzymes exhibit a certain tolerance to organic solvents (Faber, K., Biotransformations in Organic Chemistry (2001), Springer-Verlag, Heidelberg), it is also possible within the scope of the present invention to treat correspondingly pre-treated oils or gums with the enzymes.

In particularly preferred embodiments, which do not limit the scope of the present invention in any way, the method of the present invention comprises the steps Preferred Embodiment A)
 a) contacting the crude vegetable oil selected from soybean oil and/or rapeseed oil with a composition comprising a first enzyme component having at least one enzyme selected from the group consisting of phospholipase A1, phospholipase A2 and phospholipase C, and a second enzyme component having at least one enzyme selected from the group consisting of α-amylase and mannanase;
 b) separating the gums from the vegetable oil by centrifugation.

In a further preferred embodiment of the method according to the invention, a so-called pre-conditioning is carried out before step a) of the method, wherein the crude oil is mixed in a separate method step with an amount of from 1.5 to 3 ml/l of oil of organic acid, preferably citric acid. The temperature of the mixture is preferably adjusted to from 35 to 60° C., particularly preferably 48° C. After a reaction time of from 30 minutes to 2 hours, preferably 1 hour, the mixture is adjusted to a pH of 5 by addition of a stoichiometric amount of alkaline solution, preferably sodium hydroxide solution, in an amount of preferably from 0.5 to 2 mol/l, particularly preferably 1 mol/l. Only then is the procedure according to step a) of the method according to the invention followed.

Preferred Embodiment B)
 a) contacting of the crude vegetable oil selected from soybean oil and/or rapeseed oil with a composition comprising a first enzyme component having at least one enzyme selected from the group consisting of phospholipase A1, phospholipase A2 and phospholipase C, and a second enzyme component having at least one enzyme selected from the group consisting of α-amylase and mannanase, wherein it is particularly preferred if the at least one enzyme of the first enzyme component is present in immobilized form on a support;

It is particularly preferred that the enzymes of the first and/or second enzyme component are used in an aqueous phase (buffer preferably in the range pH 4.0 to 5.5, particularly preferably pH 4.0-5.0) in a concentration of from 0.05 to 5% w/v.

Contacting preferably takes place at a temperature of from 20 to 70° C., more preferably from 40 to 65° C.
 b) separating the gums from the vegetable oil by centrifugation.

This particularly preferred embodiment according to B) is combined in an embodiment that is likewise particularly preferred with a post-degumming by the addition of an organic acid and/or alkaline solution (after step b)). The temperature of the mixture is thereby preferably adjusted to from 35 to 60° C., particularly preferably 48° C. After a reaction time of from 30 minutes to 2 hours, preferably 1 hour, the mixture is adjusted to a pH of 5 by addition of an alkaline solution, preferably sodium hydroxide solution, in a concentration of preferably from 0.5 to 2 mol/l, particularly preferably 1 mol/l.

Preferred Embodiment C)
According to preferred embodiment C), instead of the crude vegetable oil, the gum phase separated by a conventional degumming method or by the method according to the invention is "contacted" with the composition according to the invention. The method is preferably carried out according to embodiment A), B) or D). This method permits, for example, the recovery of degummed oil which was separated off with the gum phase, and thus allows the oil to be recovered and accordingly leads to an indirect increase in the oil yield.

Preferred Embodiment D)
 a) contacting of the crude vegetable oil selected from soybean oil and/or rapeseed oil with a composition comprising a first enzyme component having at least one enzyme selected from the group consisting of phospholipase A1, phospholipase A2 and phospholipase C, and a second enzyme component having at least one enzyme selected from the group consisting of α-amylase and mannanase, wherein it is particularly preferred if the at least one enzyme of the first enzyme component is present in immobilized form on a support;

Contacting is thereby carried out preferably at a temperature of from 70 to 100° C., more preferably from 75 to 85° C., and using only thermally stable enzymes or enzymes whose denaturing temperature is at least 1° C., preferably 5° C., above the process temperature.

In a further preferred embodiment of the method according to the invention, a pre-conditioning is carried out before step a) of the method, wherein the crude oil is mixed in a separate method step with an amount of from 1.5 to 5 ml/l of oil of an organic acid, preferably from 1.5 to 2 ml/l of oil of citric acid. The temperature of the mixture is preferably adjusted to from 35 to 60° C., particularly preferably 48° C. After a reaction time of from 30 minutes to 2 hours, preferably 1 hour, the mixture is conditioned by addition of an alkaline solution, preferably sodium hydroxide solution, in an amount of preferably from 0.5 to 2 mol/l, particularly preferably 1 mol/l. Only then is the procedure according to step a) of the method according to the invention followed.
 b) separating the gums from the vegetable oil by centrifugation.

In addition, any phosphatidic acids which are still dissolved in the vegetable oil and have not been cleaved by the phospholipases can be reduced further by reducing the Ca and/or Mg content of the oil treated according to the method of the present invention. The above-described preferred embodiments of the method according to the invention are therefore supplemented in particularly preferred embodiments by a subsequent step in which, by again adding complexing agents such as, for example, citric acid or phosphoric acid, the content of divalent ions and, in parallel, the content of P in the oil is reduced further.

By means of the method according to the invention it is possible to reduce the phosphorus value in the crude vegetable oil significantly. The phosphorus value is thereby lowered to below 20 ppm, particularly preferably to below 10 ppm, most particularly preferably to below 4 ppm phosphorus.

Furthermore, it is possible by means of the method according to the invention to lower the calcium and magnesium content of the crude vegetable oil to below 20 ppm, particularly preferably to below 15 ppm, most particularly preferably to below 10 ppm, likewise preferably to below 8 ppm and most preferably to below 4 ppm. In a most particularly preferred embodiment, the calcium and magnesium content is lowered to below 3 ppm.

METHODS

The following analytical methods were used:
Determination of the Phosphorus Content in the Vegetable Oils The determination of phosphorus was carried out by ICP in accordance with DEV E-22.
Determination of the Calcium and Magnesium Content in the Vegetable Oils The determination of phosphorus was carried out by ICP in accordance with DEV E-22.
Determination of the Content of Free Fatty Acids (FFA)

The content of free fatty acids is determined by the consumption of sodium hydroxide or potassium hydroxide via a saponification reaction. The percentage content of free fatty acids in the oil studied is obtained. The determination was carried out in accordance with DIN 53402 (method DGF C-V 2).
Determination of the Gum Volume By means of this determination, the gum phase of enzymatically untreated and enzymatically treated gum contained in the oil is measured. A 10 ml glass centrifugal tube is heated to the working temperature of the reaction mixture, and the samples (2×2 ml) are introduced and centrifuged at 3000 rpm at a controlled temperature for at least 4 minutes in order to separate the gum phase from the oil. Samples are taken from the upper oil phases for analysis. For documentation purposes, the result of the phase formation is additionally photographed.
Determination of the Oil Content in the Gum Phase The determination of the residual oil content in the gum phase is carried out according to the Soxhlet extraction in accordance with DIN ISO 659.
Variant 1:

The amount of crude oil to be treated, from 400 to 500 g, is introduced into a 1000 ml DN120 Duran reactor, and samples are removed for analysis. The oil in the Duran reactor is heated by means of a heating plate to a temperature of from 35 to 60° C., in particular 48° C., whereby it is necessary to maintain a temperature at which the enzyme is not denatured. When the temperature has been reached, the pre-conditioning is begun. To that end, a defined amount, dependent on the amount of oil, of dilute citric acid (e.g. 450 ppm, 1.372 ml) is metered into the oil. The mixture is then mixed thoroughly for 1 minute by means of an Ultraturrax. Alternatively, the mixture is incubated for 1 hour with stirring at approximately 600 ppm until the reaction of the acid has taken place. A defined amount of sodium hydroxide solution (1 mol/l, residual amount to 2% v/v or 3% v/v minus water from acid addition and enzyme addition) is then added, and the whole is incubated for a further 10 minutes with stirring. At this point, the addition of the enzyme, of the enzyme mixture or of the immobilizate, preferably dissolved in buffer, takes place. The enzyme is stirred in, for which purpose the stirrer speed can be increased for a short time (1 minute at 900 rpm), and then stirring is continued at a lower speed.

Samples are removed at defined time intervals. The sample is removed by means of a pipette, introduced into a temperature-controlled glass centrifugal tube (temperature of the reaction mixture) and centrifuged at 3000 rpm at a controlled temperature for at least 4 minutes in order to separate the gum phase from the oil. For documentation purposes, the result of the phase formation is photographed, samples of the supernatant are taken for determination of the phosphorus, calcium and magnesium content.
Variant 2:

In a further procedure, there are added to the crude oil phospholipases and additional enzymes in a suitable combination as free enzymes or immobilized enzymes together with an aqueous phase (enzyme buffer, pH 5) 0.05 to 5% w/v. The emulsion, consisting of water, enzyme, optionally enzyme supports and oil, is mixed thoroughly. Ideally, the reaction is carried out at a controlled temperature of from 20 to 70° C., preferably from 40 to 65° C. Phase separation is then awaited, the solids are deposited or can be removed by a standard method known to the person skilled in the art, for example by centrifugation or filtration. As after-treatment, residual degumming of the oil can be carried out with dilute acid (e.g. citric acid) or alkaline solution according to a process known to the person skilled in the art as "degumming".
Variant 3:

In a further procedure, the gum phase is treated with enzymes. There are added to the gum phase, which is obtained by a process known to the person skilled in the art as "degumming", in addition to phospholipases, further enzymes. These can be dissolved in an aqueous phase or suspended in an organic solvent. The batch is ideally adjusted to a temperature of from 20 to 70° C., preferably to a temperature of from 35 to 60° C. The batch is mixed thoroughly until the process is complete. This can be verified by viscosity measurements or visually, by dissolution of the otherwise solid gum phase. A phase separation can be achieved by centrifugation, and the individual phases can be separated off. Generally, the top phase consists of the oil obtained, the middle phase consists of the phospholipids, and the bottom phase is an aqueous phase and contains the enzymes. By reusing the aqueous phase, the enzymes can be recycled and used again. Depending on the content of divalent ions, the oil or the water phase containing the enzyme must be purified of the ions by addition of complexing agents before it is used further.
Variant 4:

In a further procedure, the crude oil is brought to a high temperature, especially from 70 to 100° C., more precisely from 75 to 85° C. The crude oil is conditioned with acid and alkaline solution by the process described above, the temperature is maintained, and thermally stable enzymes are added. The further procedure is as already described. The enzyme is stirred in, for which purpose the stirrer speed can be increased for a short time (e.g. 1 minute at 900 rpm), then stirring is continued at 600 rpm until the reaction has ended. Separation of the gum phase can be carried out as described above.

EXAMPLES AND FIGURES

The invention is explained in greater detail below by means of figures and examples. It is emphasised that the examples and figures are merely of an illustrative nature and illustrate particularly preferred embodiments of the present invention. Neither the examples nor the figures limit the scope of the present invention.
The Figures Show:

FIG. 1 soybean oil: pre-conditioning with 2% total water content

Figure 2:
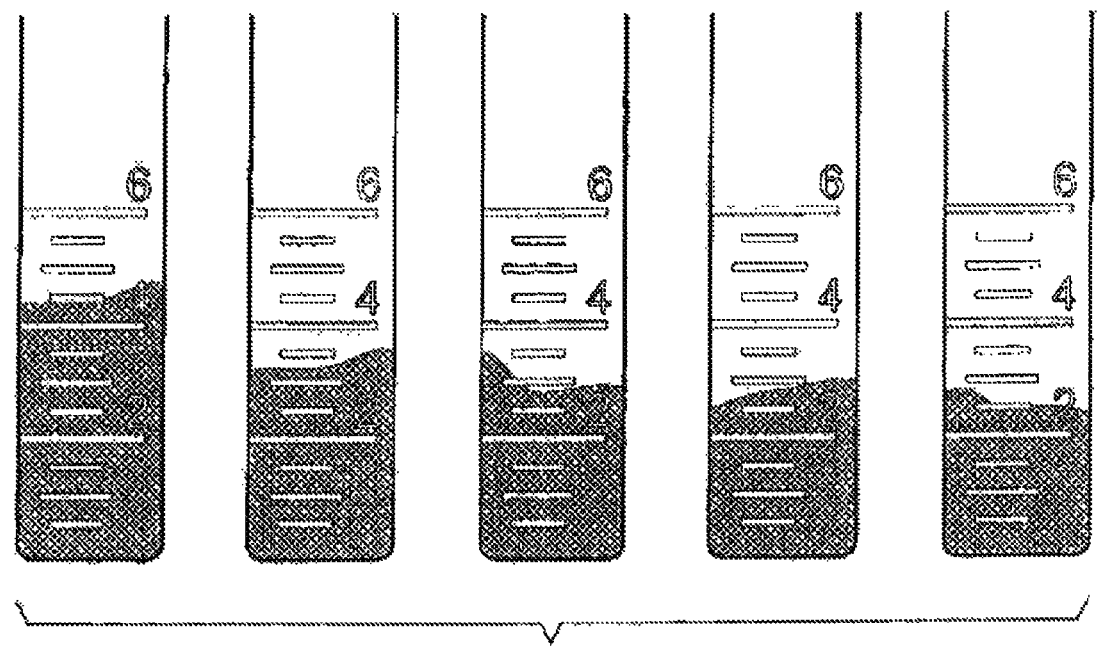
Figure 3:
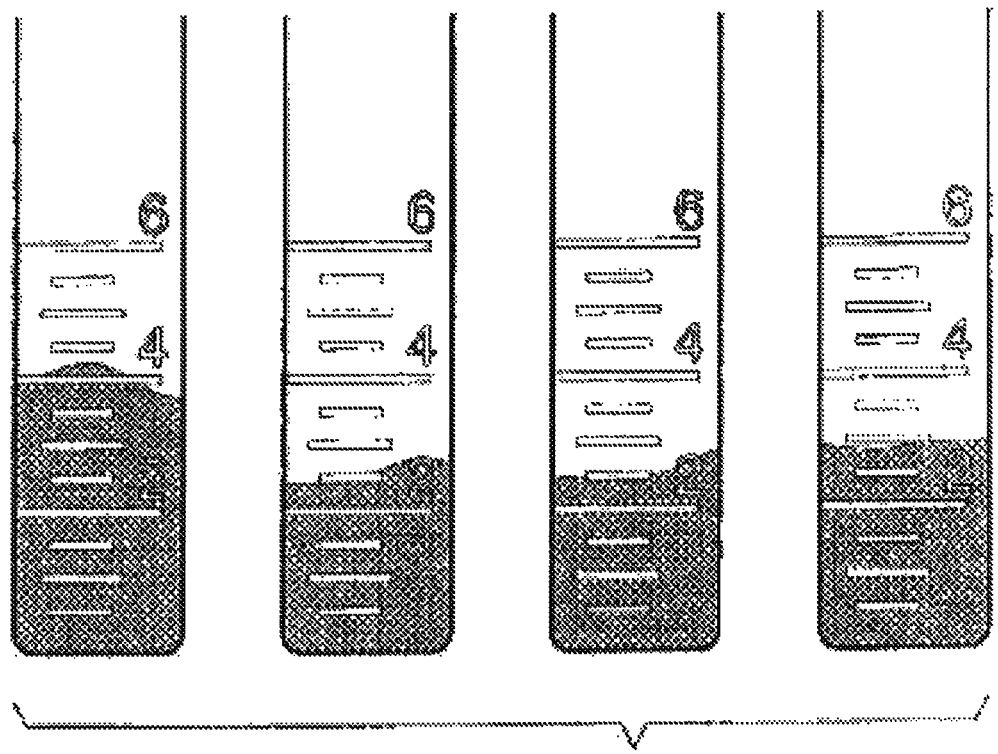
Figure 4:
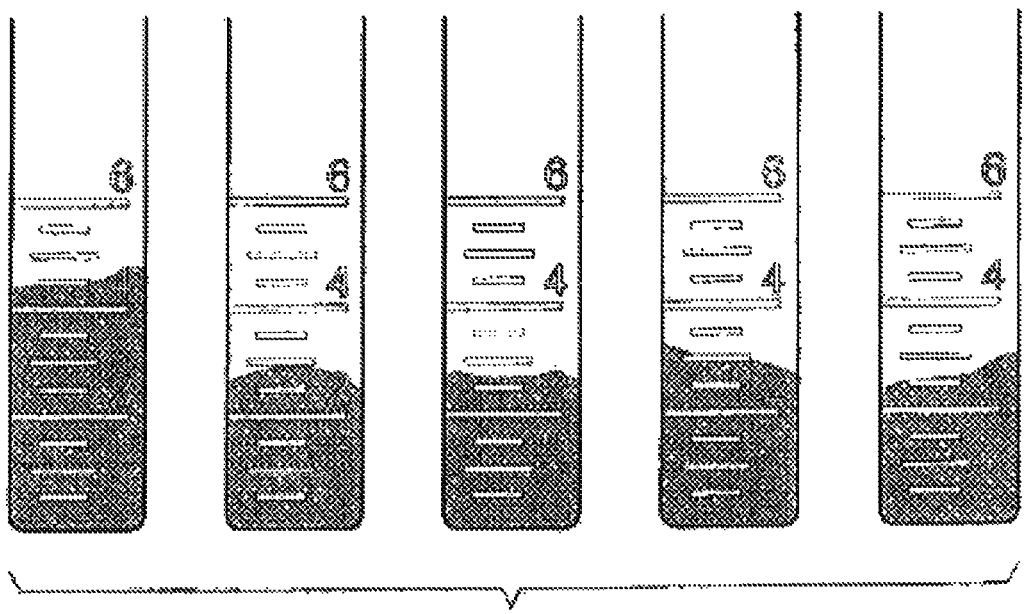
Figure 5:
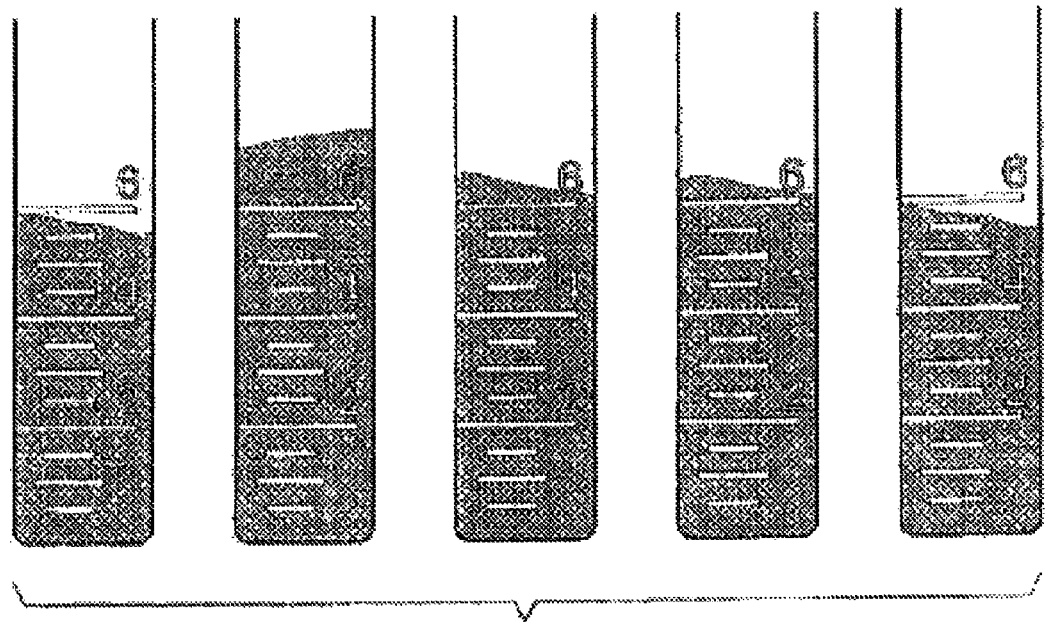
Figure 6:
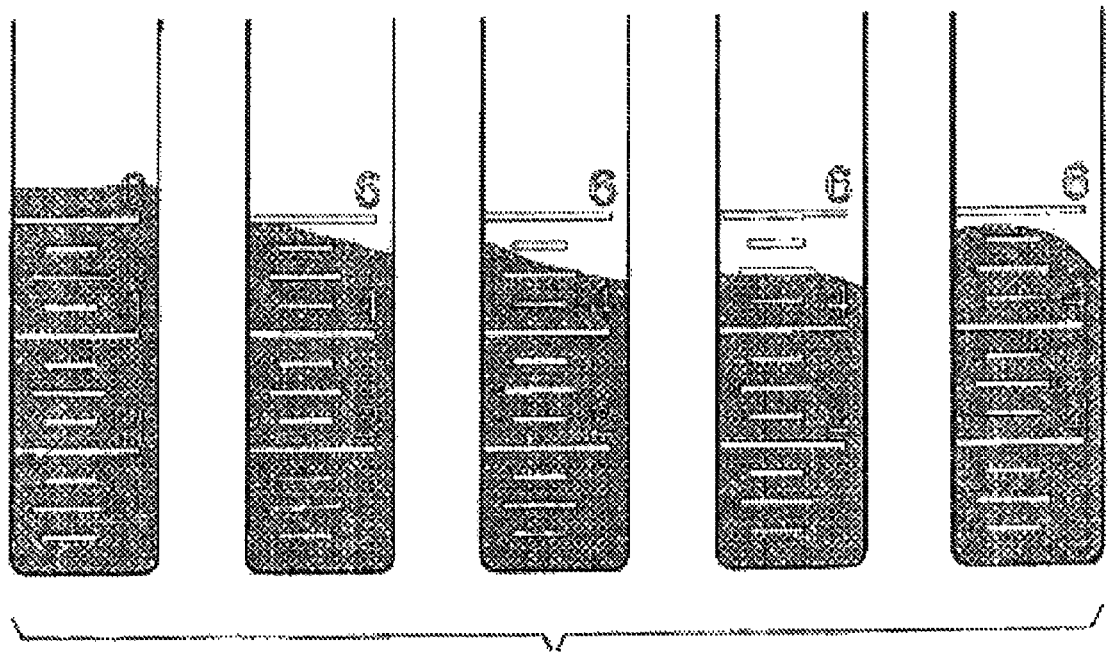
Figure 7:
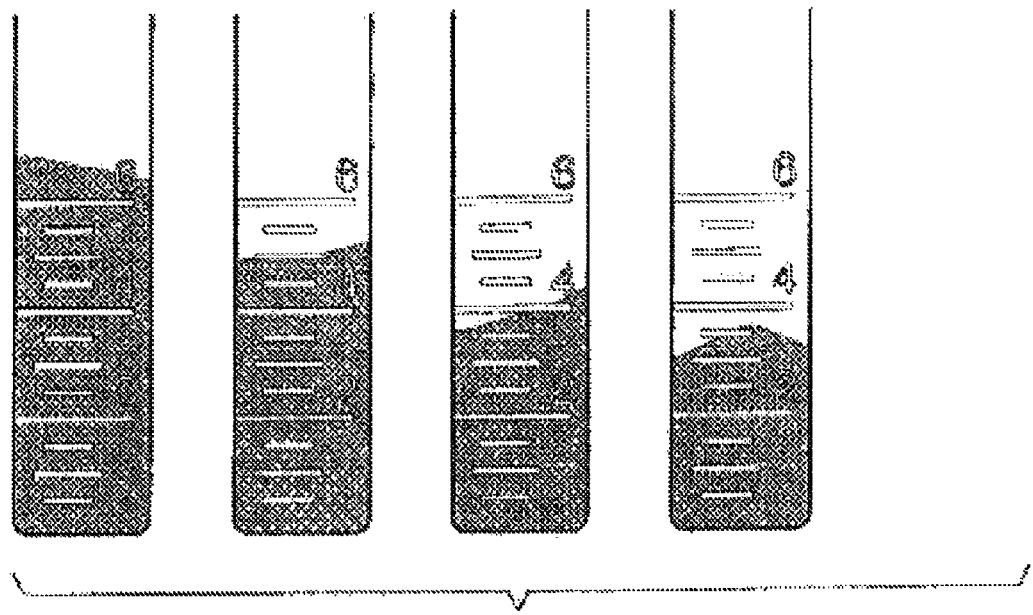
Figure 8:
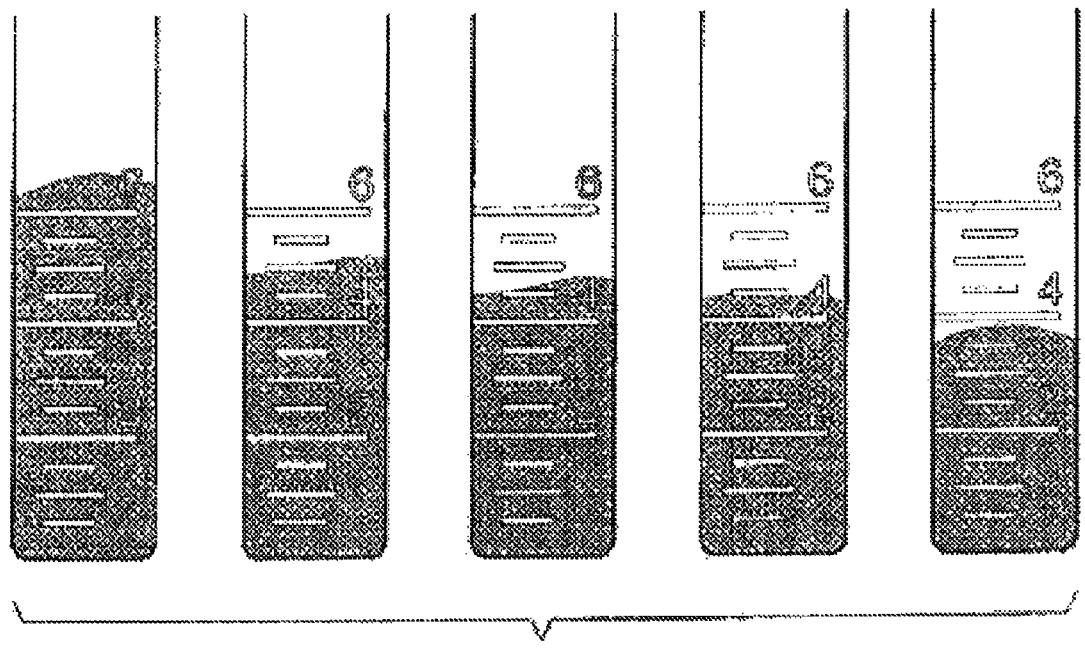

FIG. 2 soybean oil: pre-conditioning with addition of enzyme PLA1 0.3 unit/g oil and 2% total water content FIG. 3 soybean oil: pre-conditioning with addition of enzyme PLA1 0.3 unit/g oil and the enzyme α-amylase *Bacillus* spec 1 unit/g oil, 2% total water content FIG. 4 soybean oil: pre-conditioning with addition of enzyme PLA1 0.3 unit/g oil and the enzyme mannanase 0.3 unit/g oil, 2% total water content FIG. 5 rapeseed oil: pre-conditioning with 3% total water content FIG. 6 rapeseed oil: pre-conditioning with addition of enzyme PLA1 0.3 unit/g oil and 3% total water content FIG. 7 rapeseed oil: pre-conditioning with addition of enzyme PLA1 0.3 unit/g oil and the enzyme amylase PET 1 unit/g oil, 3% total water content FIG. 8 rapeseed oil: pre-conditioning with addition of enzyme PLA1 0.3 unit/g oil and the enzyme α-amylase *Aspergillus* 1 unit/g oil, 3% total water content

EXAMPLE 1

According to reaction variant 1, a soybean oil with the following starting contents was used: phosphorus 700 ppm, calcium 65.6 ppm, magnesium 62.6 ppm and a content of free fatty acids of 1%. The crude oil was subjected to pre-conditioning by means of aqueous citric acid (450 ppm) and aqueous sodium hydroxide solution (1 mol/l). Samples were taken at regular intervals (see Table 1). As comparison, the same pre-conditioning was carried out with the addition of an enzyme, phospholipase A1 from the organism *Thermomyces lanuginosus* (Sigma-Aldrich) (see FIG. 2, Table 2).

FIG. 3, Table 3, show results of the pre-conditioning with addition of the enzyme PLA1 and a further enzyme, an α-amylase from the organism *Bacillus* spec. (Sigma-Aldrich). In FIG. 4, Table 4, the same process again with addition of the enzyme PLA1 and a further enzyme, a mannanase (ASA-Spezialenzyme).

TABLE 1

Pre-conditioning with 2% total water content, phosphorus, calcium, magnesium and FFA content

| | Time [min] | | | | |
|---|---|---|---|---|---|
| | 10 | 60 | 120 | 180 | 240 |
| Ca [ppm] | 7.8 | 8.8 | 9.3 | 9.7 | 9.8 |
| Mg [ppm] | 4.1 | 3.2 | 3.1 | 3.3 | 3.2 |
| P [ppm] | 33 | 20 | 18 | 20 | 21 |
| FFA [%] | 0.75 | | | 0.76 | 0.78 |
| Gum phase [%] | 4.5 | 4.5 | 4.5 | 4.0 | 4.0 |

TABLE 2

Pre-conditioning with addition of PLA1 from *Thermomyces lanuginosus* 0.3 unit/g oil and 2% total water content, phosphorus, calcium, magnesium and FFA content

| | Time [min] | | | | |
|---|---|---|---|---|---|
| | 10 | 60 | 120 | 180 | 240 |
| Ca [ppm] | 9.6 | 9.9 | 9.3 | 8.1 | 7 |
| Mg [ppm] | 4.4 | 3.2 | 3.6 | 3 | 2.2 |
| P [ppm] | 23 | 14 | 18 | 15 | 10 |
| FFA [%] | 0.79 | | | 1.24 | 1.32 |
| Gum phase [%] | 4.8 | 3.0 | 2.8 | 2.5 | 2.5 |

TABLE 3

Pre-conditioning with addition of PLA1 0.3 unit/g oil and α-amylase from *Bacillus* spec. 1 unit/g oil, 2% total water content, phosphorus, calcium, magnesium and FFA content

| | Time [min] | | | | |
|---|---|---|---|---|---|
| | 10 | 60 | 120 | 180 | 240 |
| Ca [ppm] | 4.1 | 7.1 | 5.6 | 4.8 | 4.1 |
| Mg [ppm] | 1.9 | 2.2 | 1.8 | 1.6 | 1.4 |
| P [ppm] | 13 | 11 | 9.4 | 8.9 | 6.2 |
| FFA [%] | 0.86 | | | 1.19 | 1.16 |
| Gum phase [%] | 4.0 | 2.5 | 2.5 | | 2.5 |

TABLE 4

Pre-conditioning with addition of PLA1 0.3 unit/g oil and mannanase 0.3 unit/g oil, 2% total water content, phosphorus, calcium, magnesium and FFA content

| | Time [min] | | | | |
|---|---|---|---|---|---|
| | 10 | 60 | 120 | 180 | 240 |
| Ca [ppm] | 5.6 | 6 | 5.4 | 4.6 | 4.3 |
| Mg [ppm] | 3.5 | 2.3 | 2.1 | 1.8 | 1.7 |
| P [ppm] | 27 | 14 | 13 | 12 | 11 |
| FFA [%] | 0.75 | | | 1.19 | 1.24 |
| Gum phase [%] | 4.5 | 2.8 | 2.6 | 2.5 | 2.5 |

As is apparent from FIG. 1, the use of acid and alkaline solution on the crude oil as pre-conditioning leads to a not inconsiderable volume of the gum phase, which subsequently does not decrease substantially despite the use of a stirrer at 600 rpm. The single photo corresponds to one removed sample, samples were taken at times 10, 60, 120, 180 and 240 minutes (in each case from left to right). The associated analytical data are shown in Table 1, the phosphorus content fell after 240 minutes from 33 ppm to 21 ppm, the concentration of the divalent ions calcium and magnesium increases slightly in the case of calcium from 7.8 ppm to 9.8 ppm, the concentration of magnesium falls from 4.1 ppm to 3.2 ppm in the course of the reaction. The content of free fatty acids remains virtually unchanged. The pre-conditioning serves as a preparation reaction for the oil degumming and at the same time as a reference treatment.

In FIG. 2, a reduction of the gum phase can be seen in the course of the reaction (one photo per measurement/sample taken) when the enzyme phospholipase A1 from *Thermomyces lanuginosus* (Sigma-Aldrich) is used. The associated data and the times at which the samples were taken are shown in Table 2. Tab. 2 shows a reduction of the calcium concentration from 9.6 ppm to 7 ppm, a reduction of the magnesium concentration from 4.4 ppm to 2.2 ppm and a reduction of the phosphorus content from 23 ppm to 10 ppm, the content of free fatty acids increases from 0.79% to 1.32%. It can be concluded from the increase in the content of free fatty acids and the reduction in the phosphorus content that the PLA1 is enzymatically active and the oil degumming consequently functions successfully. The increase in the free fatty acid is an indication of the activity of the PLA1, which cleaves the fatty acids from the phospholipid molecules and also the gum phase decreases continuously. In order to open up a broader range of applications for the oil, the aim is to reduce the phosphorus content further.

FIG. 3 shows the volume of the gum phase of a pre-conditioned crude oil treated with PLA1 and additionally with alpha-amylase Bacillus spec. (Sigma-Aldrich). It is apparent from the associated analytical data in Table 3 that, surprisingly, a reduced gum phase of 2.5% is achieved after only 60 minutes. In addition, the content of free fatty acids increases from 0.86% to 1.16% and accordingly indicates the activity of the phospholipase. The phosphorus content has fallen from 700 ppm in the crude oil to 13 ppm and finally, after 240 minutes, to 6.2 ppm. The concentration of calcium varies slightly, the magnesium decreases slightly.

FIG. 4 and Table 4 show experimental data when using a further enzyme combination. There were used phospholipase A1 again and a mannanase (ASA-Spezialenzyme). It is apparent from the data that a pronounced reduction of the gum phase has occurred after only 60 minutes. The content of free fatty acids increases from 0.75% to 1.24%, the phosphorus content falls from 700 ppm in the crude oil through 27 ppm (10-minute sample) to 11 ppm after 240 minutes' treatment with the two enzymes. The concentration of divalent ions also decreases over the entire course of the reaction. The results prove that the addition of a further glycoside-cleaving enzyme leads, surprisingly, to a more rapid and more pronounced reduction of the gum phase.

EXAMPLE 2

According to reaction variant 1, a rapeseed oil with the following starting contents was used: phosphorus 1150 ppm, calcium 370 ppm, magnesium 146 ppm and a content of free fatty acids of 1.95%. The crude oil was subjected to pre-conditioning by means of aqueous citric acid (1000 ppm) and aqueous sodium hydroxide solution (4 mol/l). Samples were taken at regular intervals (see Table 5). As comparison, the same pre-conditioning was carried out with the addition of an enzyme, phospholipase A1 from the organism *Thermomyces lanuginosus* (Sigma-Aldrich) (see FIG. 6, Table 6). FIG. 7, Table 7, show results of the pre-conditioning with addition of the enzyme PLA1 and a further enzyme, an amylase PET from the organism *Bacillus subtilis* (ASA Spezialenzyme GmbH). In FIG. 8, Table 8, the same process again with addition of the enzyme PLA1 and a further enzyme, an α-amylase from *Aspergillus oryzae* (Sigma-Aldrich).

TABLE 5

Pre-conditioning with 3% total water content, phosphorus, calcium, magnesium and FFA content

| | Time [min] | | | | |
|---|---|---|---|---|---|
| | 10 | 60 | 120 | 180 | 240 |
| Ca [ppm] | 76 | 11 | 9.5 | 9.4 | 9.5 |
| Mg [ppm] | 31 | 2.8 | 1.7 | 1.6 | 1.7 |
| P [ppm] | 247 | 20 | 14 | 13 | 14 |
| FFA [%] | 1.73 | | | 1.68 | 1.72 |
| Gum phase [%] | 5.8 | 6.5 | 6.0 | 6.0 | 5.8 |

TABLE 6

Pre-conditioning with addition of PLA1 from *Thermomyces lanuginosus* 0.3 unit/g oil and 3% total water content, phosphorus, calcium, magnesium and FFA content

| | Time [min] | | | | |
|---|---|---|---|---|---|
| | 10 | 60 | 120 | 180 | 240 |
| Ca [ppm] | 26 | 9.7 | 8.7 | 7.9 | 7.9 |
| Mg [ppm] | 9.7 | 2.1 | 1.8 | 1.4 | 1.5 |
| P [ppm] | 82 | 17 | 15 | 12 | 12 |
| FFA [%] | 1.76 | | | 2.35 | 2.14 |
| Gum phase [%] | 6.5 | 5.6 | 5.0 | 4.5 | 5.5 |

TABLE 7

Pre-conditioning with addition of PLA1 0.3 unit/g oil and amylase PET 1 unit/g oil, 3% total water content, phosphorus, calcium, magnesium and FFA content

| | Time [min] | | | | |
|---|---|---|---|---|---|
| | 10 | 60 | 120 | 180 | 240 |
| Ca [ppm] | 16 | 14 | 13 | 12 | 11 |
| Mg [ppm] | 4.8 | 2.8 | 2.7 | 2.4 | 1.9 |
| P [ppm] | 38 | 21 | 19 | 15 | 13 |
| FFA [%] | 1.84 | | | 2.24 | 2.20 |
| Gum phase [%] | 6.9 | 5.3 | 4.0 | 3.8 | 3.4 |

TABLE 8

Pre-conditioning with addition of PLA1 0.3 unit/g oil and an α-amylase from *Aspergillus* unit/g oil, 3% total water content, phosphorus, calcium, magnesium and FFA content

| | Time [min] | | | | |
|---|---|---|---|---|---|
| | 10 | 60 | 120 | 180 | 240 |
| Ca [ppm] | 39 | 12 | 9.3 | 8.1 | 7.1 |
| Mg [ppm] | 15 | 3.2 | 2.2 | 1.7 | 1.3 |
| P [ppm] | 130 | 25 | 19 | 14 | 10 |
| FFA [%] | 1.92 | | | 2.49 | 2.45 |
| Gum phase [%] | 6.5 | 5.1 | 4.6 | 4.4 | 3.6 |

As is apparent from FIG. 5, the use of acid and alkaline solution on the crude oil as pre-conditioning leads to a considerable volume of the gum phase, which subsequently does not decrease substantially despite the use of a stirrer at 600 rpm. The single photo corresponds to one removed sample, samples were taken at times 10, 60, 120, 180 and 240 minutes (from left to right). The associated analytical data are shown in Table 5, the phosphorus content fell after 240 minutes from 247 ppm to 14 ppm, the concentration of the divalent ions calcium and magnesium decreases in the case of calcium from 76 ppm to 9.5 ppm, the concentration of magnesium falls from 31 ppm to 1.7 ppm in the course of the reaction. The content of free fatty acids remains virtually unchanged. The pre-conditioning serves as a preparation reaction for the oil degumming and at the same time as a reference treatment.

In FIG. 6, when the enzyme phospholipase A1 from *Thermomyces lanuginosus* (Sigma-Aldrich) is used, a slight decrease of the gum phase in the course of the reaction can be seen (one photo per measurement/sample taken) to approximately 0.5% at the end of the reaction. The associated data and the times at which the samples were taken are shown in Table 6. The content of free fatty acids increases from 1.76% to 2.14%. The increase of the free fatty acid is an indication of the activity of the PLA1, which cleaves the fatty acids from the phospholipid molecules. Surprisingly, it has now been found that, by adding a glycoside-cleaving enzyme to the phospholipase, the gum phase of the rapeseed oil treatment is reduced significantly, see FIGS. 7 and 8 and the associated data from Tables 7 and 8. In FIG. 7, an amylase PET (ASA Spezialenzyme) was added, in FIG. 8 an α-amylase from *Aspergillus oryzae* (Sigma-Aldrich) was added. Here too, the results prove that the addition of a further glycoside-cleaving enzyme leads, surprisingly, to a more rapid and more pronounced reduction of the gum phase, which means an increase of the oil yield.

TABLE 9

Rapeseed oil: Total oil yield of the reactions from Example 2 after Soxhlet extraction of the gum phase

| | Oil yield [%] |
|---|---|
| H3Cit (citric acid) | 96 |
| PLA1 | 97 |
| PLA1 + amylase PET | 98.5 |
| PLA1 + α-amylase *Aspergillus* | 98 |

Table 9 shows the total oil yield (rapeseed oil) of the reactions from Example 2 after Soxhlet extraction of the gum phase. It is apparent that a glycoside-cleaving additional enzyme in combination with the PLA1 increases the oil yield considerably from a yield of 96% in the case of treatment without enzyme (H3Cit) or a yield of 97% in the case of treatment with the enzyme PLA1 alone, to 98% (PLA1+α-amylase *Aspergillus*) and 98.5% (PLA1+amylase PET), respectively.

Approximately 22.1 million tonnes of rapeseed oil are produced worldwide each year (USDA FAS—2010). By increasing the oil yield by 2 to 2.5% by means of the enzymatic process described here, approximately 440,000 to 550,000 tonnes more rapeseed oil can be produced per year.

What is claimed is:

1. A method for reducing the emulsifiability of vegetable oil in aqueous phases, comprising the steps:
    contacting crude vegetable oil with water and/or acid to yield a pre-conditioned oil, said preconditioned oil comprising gum(s);
    contacting said preconditioned oil with a composition comprising a first enzyme component, and a second enzyme component, said first enzyme component comprising at least one phospholipid-cleaving enzyme, and said second enzyme component comprising at least one non-phospholipid-cleaving enzyme, wherein the second enzyme component is an α-amylase; and separating the gum(s) from said preconditioned oil.

2. The method according to claim 1, wherein the first enzyme component is selected from the group consisting of phospholipase A1, phospholipase A2, phospholipase C, phospholipase B, phospholipase D and acyltransferase.

3. The method according to claim 2, wherein the phospholipase A1 originates from *Thermomyces lanuginosus, Fusarium oxysporium, Aspergillus oryzae, Bacillus cereus, Bacillus subtilis, Clostridium perfringens, Listeria monocytogenes, Pseudomonas*species, porcine pancreas or bovine pancreas; and/or independently the phospholipase A2 originates from porcine pancreas, bovine pancreas, *Streptomyces violaceoruber, Naja mossambica, Thermomyces lanuginosus, Fusarium oxysporium, Aspergillus oryzae, Bacillus cereus, Bacillus subtilis, Clostridium perfringens, Listeria monocytogenes* or *Pseudomonas*species; and/or independently the phospholipase C originates from *Bacillus cereus, Clostridium perfringens, Listeria monocytogenes, Thermomyces lanuginosus, Fusarium oxysporium, Aspergillus oryzae, Bacillus cereus* or *Pseudomonas* species; and/or independently the phospholipase B originates from *Thermomyces lanuginosus, Fusarium oxysporium, Aspergillus oryzae, Bacillus cereus, Bacillus subtilis, Clostridium perfringens, Listeria monocytogenes, Pseudomonas* species, porcine pancreas or bovine pancreas.

4. The method according to claim 2, wherein the phospholipase A1originates from *Thermomyces lanuginosus* or *Fusarium oxysporium*, and/or independently the phospholipase A2 originates from porcine pancreas, bovine pancreas, *Streptomyces violaceoruber* or *Naja mossambica*, and/or independently the phospholipase C originates from *Bacillus cereus, Clostridium perfringens* or *Listeria monocytogenes*.

5. The method according to claim 1, wherein the alpha-amylase cleaves at least one of an alpha(1-4)glycosidic bond, an alpha(1-2)glycosidic bond, an alpha(1-6)-glycosidic bond, or an alpha(1-3)glycosidic bond.

6. The method according claim 1, wherein the alpha-amylase is an alpha-amylase from *Bacillus* sp., *Bacillus subtilis, Bacillus licheniformis, Bacillus megaterium, Bacillus amyloliquefaciens, Bacillus stearothermophilus, Pseudomonas aeroginosus, Pseudomonas fluorescens, Aspergillus oryzae*, or *Aspergillus niger*.

7. The method according to claim 1, wherein the ratio of the enzyme activity of the first enzyme component to the enzyme activity of the second enzyme component is about 0.01:6 units/g oil to 6:0.01 units/g oil.

8. The method according to claim 1, wherein the first and/or second enzyme component is/are present in immobilized form.

9. The method according to claim 1, wherein the first and/or second enzyme component is also separated from the preconditioned oil at the same time as the gums.

10. The method according to claim 1, wherein vegetable oil gum is used instead of vegetable oil.

11. The method according to claim 1, wherein the vegetable oil is canola oil, rapeseed oil, soybean oil or a combination thereof.

12. A method for reducing the emulsifiability of vegetable oil in aqueous phases, comprising the steps:
    contacting crude vegetable oil with water and/or acid to yield a pre-conditioned oil, said preconditioned oil comprising gum(s), wherein said crude vegetable oil is canola oil, rapeseed oil, soybean oil or a combination thereof;
    contacting said preconditioned oil with a composition comprising:
        a first enzyme component, wherein the first enzyme component is selected from the group consisting of phospholipase A1, phospholipase A2, phospholipase C, phospholipase B, phospholipase D and acyltransferase; and
        an α-amylase, wherein the alpha-amylase is an alpha-amylase from *Bacillus* sp., *Bacillus subtilis, Bacillus licheniformis, Bacillus megaterium, Bacillus amyloliquefaciens, Bacillus stearothermophilus, Pseudomonas aeroginosus, Pseudomonas fluorescens, Aspergillus oryzae*, or *Aspergillus niger*; and
    separating the gum(s) from said preconditioned oil wherein the ratio of the enzyme activity of the first enzyme component to the enzyme activity of the α-amylase is about 0.01:6 units/g oil to 6:0.01 units/g oil.

* * * * *